United States Patent
Fuhr et al.

[11] Patent Number: 6,056,861
[45] Date of Patent: May 2, 2000

[54] PROCESS AND DEVICE FOR GENERATING RESONANCE PHENOMENA IN PARTICLE SUSPENSIONS

[75] Inventors: Günter Fuhr; Jan Gimsa; Torsten Müller; Thomas Schnelle, all of Berlin, Germany

[73] Assignee: Gunter Fuhr, Berlin, Germany

[21] Appl. No.: 09/077,334

[22] PCT Filed: Nov. 27, 1996

[86] PCT No.: PCT/EP96/05244

§ 371 Date: Jul. 27, 1998

§ 102(e) Date: Jul. 27, 1998

[87] PCT Pub. No.: WO97/20210

PCT Pub. Date: Jun. 5, 1997

[30] Foreign Application Priority Data

Nov. 27, 1995 [DE] Germany .......................... 195 44 127

[51] Int. Cl.$^7$ .................................................. G01N 27/26
[52] U.S. Cl. .......................... 204/547; 204/643; 204/600; 204/450
[58] Field of Search .................................... 204/547, 643, 204/450, 458, 600, 609, 400; 205/775

[56] References Cited

U.S. PATENT DOCUMENTS

| | | |
|---|---|---|
| 4,326,934 | 4/1982 | Pohl . |
| 4,390,403 | 6/1983 | Batchelder . |
| 5,059,294 | 10/1991 | Lizardi . |
| 5,084,157 | 1/1992 | Clark et al. . |
| 5,102,524 | 4/1992 | Dutertre . |
| 5,106,468 | 4/1992 | Chimenti . |
| 5,173,164 | 12/1992 | Egen et al. . |
| 5,645,702 | 7/1997 | Witt et al. ................................ 204/501 |

FOREIGN PATENT DOCUMENTS

| | | |
|---|---|---|
| 136895 | 1/1979 | Germany . |
| 4034697A1 | 5/1992 | Germany . |
| 4400955A1 | 1/1994 | Germany . |
| 9111262 | 12/1991 | WIPO . |

OTHER PUBLICATIONS

Herbert A. Pohl, "Dielectrophoresis", Cambridge University Press (1978) (relevante Auszuge). Date of Publication is Unknown.

W.M. Arnold et al., "Rotating–Field–Induced Rotation and Measurement of the Membrane Capacitance of Single Mesophyll Cells", Z. Naturforsch. 37c, 908–915 (1982). Date of Publication is Unknown.

Masao Washizu et al., "Movement of Blood Cells in Liquid by Nonuniform Traveling Field", Bd. 24, Nr. 2, Marz 1988, S. 217–222. Date of Publication is Unknown.

Thomas Schnell et al., "Three–Dimensional electric field traps for manipulation of cells—calculation and experimental verification", Biochim. Biophys. Acta 1157, 127–140 (1993). Date of Publication is Unknown.

Rolf Hagerdorn et al., "Traveling–wave dielectrophoresis of microparticles", Department of Biology, Humboldt–University of Berlin, 49–54 (1992). Date of Publication is Unknown.

(List continued on next page.)

Primary Examiner—Jill Warden
Assistant Examiner—Alex Noguerola

[57] ABSTRACT

A method and a device for position and/or type-selective control of the position and/or change of position of suspended particles in a multielectrode system by the effect of polarization forces that are induced in the particles by alternating electric fields in the multielectrode system, which particles comprise biological or synthetic objects with dimensions essentially corresponding to those of biological cells or cell organelles, viruses or macromolecules, base on the fact that the multielectrode system forms with the particle suspension an electrical network, in which means of resonance are provided for creating a resonant increase or damping of the field strength of the alternating electric fields at certain frequencies in at least one locally demarcated region of the multielectrode system.

19 Claims, 8 Drawing Sheets

OTHER PUBLICATIONS

Gunter Fuhr et al., "Dielectric Spectroscopy of Chloroplasts Isolated from Higher Plants–Characterization of the Double–Mambrane System", Plant Cell Physiol. 31(7), 975–985 (1990). Date of Publication Known.

W.M. Arnold et al., "Electro–Rotation: Development of a Technique for Dielectric Measurements on Individual Cells and Particles", Journal of Electrostatics 21, 151–191 (1988). Date of Publication is Unknown.

J. Gimsa et al., "Physical Characterization of Biological Cells", Verlag Gesundheit GmbH, Berlin 296–323 (1991). Date of Publication Unknown.

Masao Washizu et al., "Handling Biological Cells Using a Fluid Integrated Circuit", IEEE Trans. IA, 25(4), 352–359 (1990). Date of Publication is Unknown.

Felix M. Moesner et al., "Electrostatic Devices for Particle Micro–Handling", Bd. 2, 1302–1309 (1995).

PROCESS AND DEVICE FOR GENERATING RESONANCE PHENOMENA IN PARTICLE SUSPENSIONS

This application claims the benefit under 35 U.S.C. §371 of prior PCT International Application No. PCT/EP96/05244 which has an International filing date of Nov. 27, 1996 which designated the United States of America, the entire contents of which are hereby incorporated by references.

BACKGROUND OF THE INVENTION

The invention concerns a method and a device for position and/or type-selective control of the position and/or change of position of suspended particles in a multielectrode system with the features of the preambles of patent claims 1 or 9, and especially planar and three-dimensional microelectrode configurations in semiconductor chip size, or a method of moving, holding, measuring or sorting suspended artificial or living particles (e.g. cells) or organic particles of microscopic size in fluids. For individual handling and/or characterization of such particles, and especially for directing them in a field gradient or traveling electric field, dielectric polarization forces are used that are generated by alternating electric fields and amplified by resonance phenomena.

Two basic principles are currently known by which electrical handling and characterization of individual objects can be performed: 1. the generation of field gradients in high-frequency alternating fields (Pohl, H. P., Dielectrophoresis, Cambridge University Press [1978]) and 2. application of rotating fields with a tunable rotation frequency (Arnold, W.-M. and Zimmermann, U., Z. Naturforsch. 37c, 908 [1982]). Related fields, but not included here, like electrophoresis and other direct-voltage techniques can also be used in part for the named particles but are not comparable in their effectiveness.

The first principle mentioned above leads to asymmetric polarization of microparticles, producing, (depending on the nature of the polarization, motion in the direction of higher or lower field strength. This response is termed positive or negative dielectrophoresis (Pohl, H. P., Dielectrophoresis, Cambridge University Press [1978]) and has been used for more than 30 years to move and separate suspended dielectric bodies and cells. In recent years dielectrophoretic principles have come into wider use in the biological/medical field through the introduction of semiconductor microelectrode systems (Washizu, M. et al., IEEE Trans. IA, 25(4), 352 [1990]; Schnelle, T. et al., Biochim. Biophys. Acta 1157, 127 [1993]).

The second of the principles mentioned above, the application of rotating fields of variable frequency (this category also includes linear traveling fields (Hagedorn, R. et al., Electrophoresis 13, 49 [1992])), is used to characterize the passive electrical features of individual suspended particles, and especially of cells (Arnold, W.-M. and Zimmermann, U., Z. Naturforsch. 37c, 908 [1982]; Fuhr, G. et al., Plant Cell Physiol. 31, 975 [1990]). The principle can be summarized as follows. A particle is located in a circular electrode configuration with a rotating field with a speed of a few hertz to several hundred megahertz. Because of the viscosity of the solution, it reacts like the rotor of a dielectric asynchronous motor. In the case of cells with their extremely complex structure (cell wall, membrane, organelles, etc), the frequency spectra of the rotation (particle rotation as a function of the rotation frequency of the field) allow far-reaching conclusions about the physiology and the characteristics of individual components of the same (Arnold, W.-M. and Zimmermann, U., J. Electrostat. 21, 151 [1988]; Gimsa et al. in Schutt, W., Klinkmann, H., Lamprecht, I., Wilson, T., Physical Characterization of Biological Cells, Verlag Gesundheit GmbH, Berlin [1991]).

All alternating electric field methods make use of polarization forces resulting from the relaxation of induced charges. What is of disadvantage is the half width of the dielectric dispersions, which are approximately of the order of a frequency decade (Pohl, H. P., Dielectrophoresis, Cambridge University Press [1978]; Arnold, W.-M. and Zimmermann, U., J. Electrostat. 21, 151 [1988]). This means that differentiation or differentiated movement of different particles requires relatively large differences in the structure or the dielectric characteristics. A further problem, especially as the particle radius reduces, is that other forces (local flow, thermal motion, etc) gain in influence and even exceed the polarization forces at a particle radius of less than a micrometer. With colloidal particles, where polarizability is far less than that of biological cells, the disadvantage is that relatively high control voltages (three to ten times as high) have to be applied to achieve the same force effects.

This is the reason why the two principles mentioned above could only be used to date for relatively large particles, and why a possibility has long been sought of amplifying the field effects.

SUMMARY OF THE INVENTION

The object of the present invention is to show an improved method for local and/or type-selective control of the position and/or change of position of suspended particles in a multielectrode system and a device for its implementation, with which, without increasing the field amplitude, substantial amplification of the polarization forces is achieved at previously determined frequencies and the natural frequency width of the force effects, resulting from the dielectric dispersions, is markedly reduced or narrowed down. This object is achieved by a method and a device with the features of patent claims 1 or 9. Advantageous embodiments of the invention are defined in the subsidiary claims. Preferred uses of the invention are stated in claim 20.

In particular electrode systems are to be shown in which amplification of the polarization forces in locally limited areas (typically a few hundred micrometers and less in all three dimensions) is produced on the basis of frequency selective amplification of the electric field forces by generating spatially limited resonances.

The multielectrode systems according to the invention are, in the first place, open oscillating circuit systems in which, at the frequency interval considered ($\geq 100$ kHz), no resonance phenomena would be expected. As part of the present invention it was nevertheless found, surprisingly enough, that the open oscillating circuit systems form closed networks through the particle suspensions, in which resonances can be achieved especially in low frequency regions.

The use of extremely miniaturized electrode systems (typically in the micrometer range in two dimensions, a few millimeters and less in the third dimension) and their planar or three-dimensional configuration or interconnection with capacitive, inductive and resistive elements plus the application of high-frequency electric fields (e.g. f>10 kHz) of an amplitude in the mV to V range allow the generation of local resonance phenomena within the microstructure that increase the field amplitude at these points by a multiple.

Since the polarization forces are proportional to the square of the field strength, multiplied particle repelling or attracting forces appear (two to 1000 times and more), that can be used to achieve the above stated object.

According to the invention the microelectrodes are arranged, selected in their geometry or coated or underlaid with materials so that predefined capacitive, inductive and resistive components determine the electrical high-frequency characteristics of each electrode with the suspension medium surrounding it. The components of the individual electrodes, after electrical connection through the particle suspension, form networks with resonance phenomena that are arranged precisely on a substrate (glass, silicon, etc) so that the field strengths are increased by resonance where particles are to be handled or measured, e.g. in the electrode interspace. The generation of resonances can be supported or shifted and determined in frequency by integrating further components or connecting external capacitors, inductors and resistors. Calibration of the resonance frequency is possible during operation. This effect can be used both for particle orientation, movement and holding and for dielectric measurement.

The resonance effects can be applied selectively, just for a certain spectral component of the driving signal, by using different signal shapes for the electrode control. Possible are sinusoidal, squarewave, triangular or other periodic and aperiodic signals. Depending on the extent to which the Fourier series have fundamentals and harmonics for describing these signals, resonances of the fundamental as well as its harmonics can be used.

Local restriction of the resonances to one or more areas of less than a cubic millimeter is determined by the design of the ends of the electrodes (circular, series, facing, etc) and the nature of the suspension solution. From an electronic viewpoint these configurations are to be seen as systems not terminated with a defined impedance. As will be shown in the examples however, electrode configurations can be found in which the terminating impedance of the solution merely determines the amplitude of the resonances, not their frequency.

In contrast to the resonance effects known in electronics, the polarized particles and cells of the invented method are to be regarded as sample bodies for the resonance-related increase of field strength inside the dielectric (fluid) of a capacitor, whose presence in turn influences the resonance phenomena of the system and can be utilized by tuning the resonant frequency for particle separation, collection and holding.

Especially effective is the integration of tunable capacitive, inductive and/or resistive elements with which individual electrodes can be matched individually or resonances defined in frequency and altered by programs. The advantage of this is that, while keeping the same electrode configuration, polarization forces can be amplified or damped from the exterior as a function of frequency. This effect can be used to separate individual particle classes with the same or similar dielectric characteristics from other particle types.

The following principles can be applied for calibrating and controlling the required resonant effect:

1. Active tuning of the oscillating circuit elements, e.g. capacitors, inductors and resistors.
2. Application of two or more fields of the same or opposing sense of rotation of different frequency.
3. Application of fields as in point 2 with different but adjustable amplitude.
4. Application of fields as in point 2 with different exposure time of the fields.
5. Application of fields as in point 2 with calibration between their frequencies.
6. Application of periodic signals with different harmonic content.
7. Combination of the principles stated in points 1 through 6.

In practice the generation of resonances in microelectrode systems according to the invention can be produced as follows:

It is possible to set the conditions for resonance by dimensioning/shaping the electrodes while allowing for the concrete requirements of microstructuring. Thus the electrode system shown in FIG. 1 for example, ie the corresponding equivalent circuit diagram in FIG. 2, can be analyzed and modeled by common methods of computer-aide network analysis (computation of voltages at random points in the network).

The necessary characteristics of the electrode system can also be determined by experiment. For this purpose a network (equivalent circuit diagram) corresponding to an electrode system is realized and measured, while any extra external capacitors and/or inductors are added and tuned. This procedure is preferred especially if the number of electrodes is relatively high (e.g. $\leq 8$).

In the implementation of values determined by experiment, there are again two practicable procedures. Firstly, it is possible when processing the electrodes, using semiconductor technology for example, to integrate the calculated switching elements on the chip. The advantage of this is that the capacitive/inductive elements themselves take on dimensions in the micrometer region and have virtually no reaction on the circuit of the generator. Secondly, the chip can be wired with external components. The disadvantages of this are the reduced design possibilities and the but indirect effect of the components in the electrode space because of their input leads.

Finally it is possible to integrate controllable components on the chip in the multielectrode system. These include in particular active components like switching diodes, transistors and controllable variable-capacitance diodes etc. The advantage here is that the resonances can be tuned one after the other, allowing external computer control of the system. A further variant in this context is the use of mechanical means of setting that make use of magnetic or piezoelectric effects (e.g. field influence in FET).

The processing of planar electrode structures using semiconductor technology offers a variety of possibilities, because capacitive, inductive and resistive elements in the micrometer region can be implemented. The advantage of this configuration, compared to external wiring, is that the networks can be arranged so that the electrodes are not wired uniformly but in a definable manner. This principle also assists considerably in spatial limiting of the resonance phenomenon on the chip or the microstructured surface.

The multielectrode configuration according to the invention can comprise two, three, four or more electrodes for example. It can be enclosed in chip form in a ceramic package with electric leads.

Preferred examples of design of the invention are explained in more detail below with reference to the accompanying figures.

Four electrodes 10$a$–$d$, 12$a$–$d$, 13$a$–$d$ (black) are shown, enclosing a central area 14 with a suspended particle of about 100 $\mu$m diameter or less. The electrodes are designed so that capacitive and inductive components appear when they are driven by alternating voltage. By underlaying a widened metal layer 12$a$–$d$ (e.g. gold, 1 $\mu$m thick, 100 $\mu$m wide) with a dielectric 11$a$–$d$ (dielectric constant as high as possible), a capacitor is formed that is taken to ground (here the schematically illustrated substrate 16). The meander-shaped leads 13$a$–$d$ increase the inductances of the electrode leads. As a result of the way in which the electrodes are faced and the electrical connection of the electrode ends in the central area 14 through the suspension solution, the inductive, capacitive and resistive electrode components are linked into an electronic network. Depending on whether the electrodes are of identical or differing design, resonances can be generated in the central area 14 of the electrodes that increase the field forces on the particle by a multiple compared to the same driving amplitude of the electrodes without the described configuration (in electrolyte solutions that can mean values between >1 and 1000 or more for example). The conductivity of the suspension solution damps the height of the resonance however.

Figure 1:
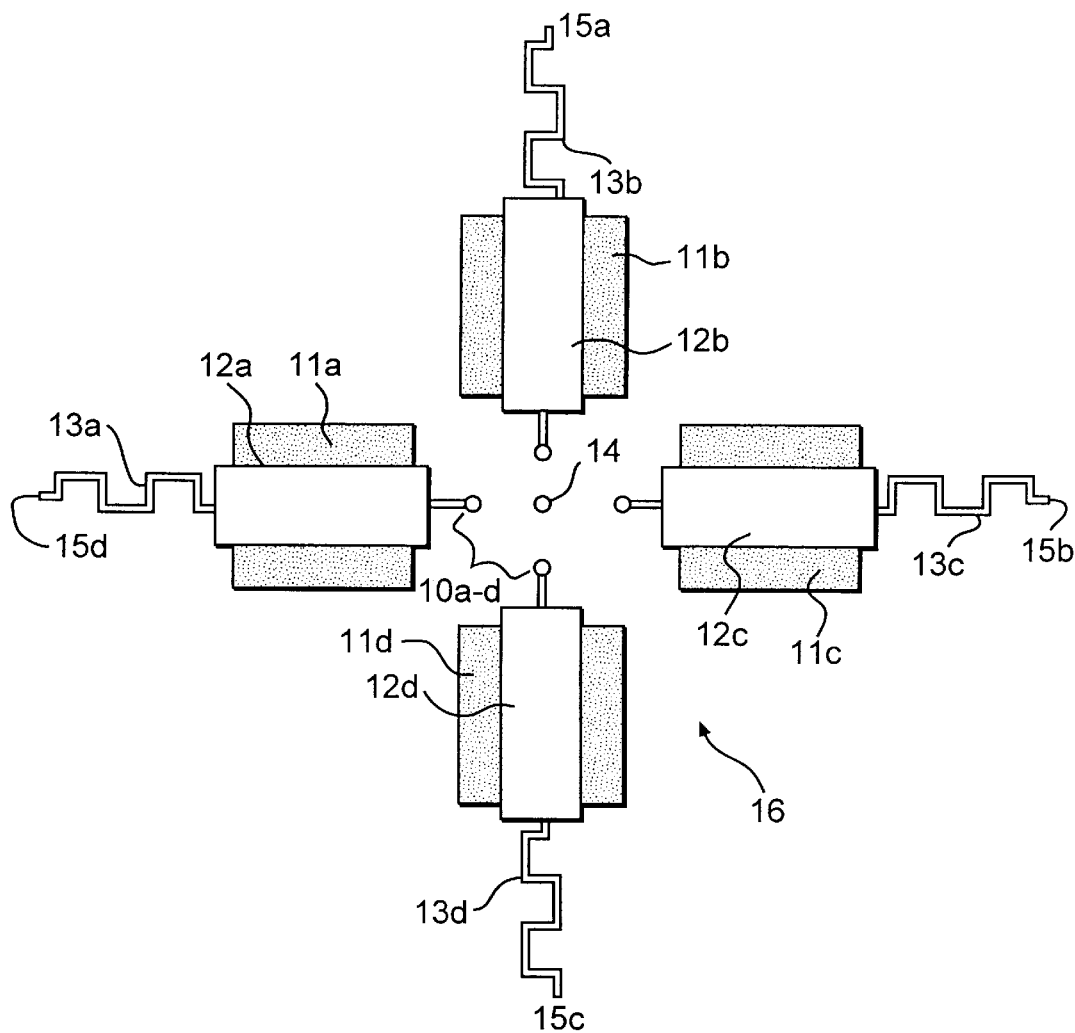
FIG. 1 illustrates a section from a microstructured surface.
Figure 2:
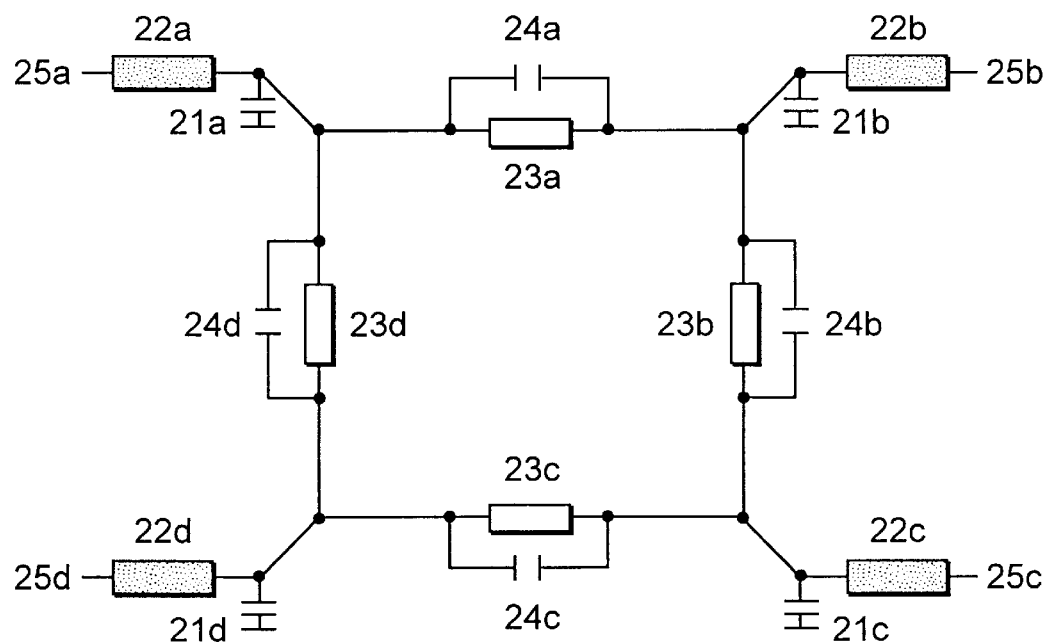
FIG. 2 illustrates a simplified equivalent circuit diagram for the electrode configuration shown in FIG. 1.

FIG. 2 is a simplified equivalent circuit diagram for the electrode configuration shown in FIG. 1. It can be seen that the interconnection of the lead capacitances 21$a$–$d$, of the electrode inductances 22$a$–$d$, of the suspension solution resistances 23$a$–$d$ between the electrodes and the capacitances between the electrodes 24$a$–$d$ produces a network with four input poles 25$a$–$d$. This system, driven by alternating voltage (pole 25$a$–phase=0°, pole 25$b$–phase=180°, pole 25$c$ phase=0°, pole 25$d$–phase=180°) but also when excited by a rotating field (pole 25$a$–phase=0°, pole 25$b$–phase=90°, pole 25$c$–phase=180°, pole 25$d$–phase=270°), shows a marked resonant response. The frequency can be defined very precisely by the inductances and capacitances.

Figure 3:
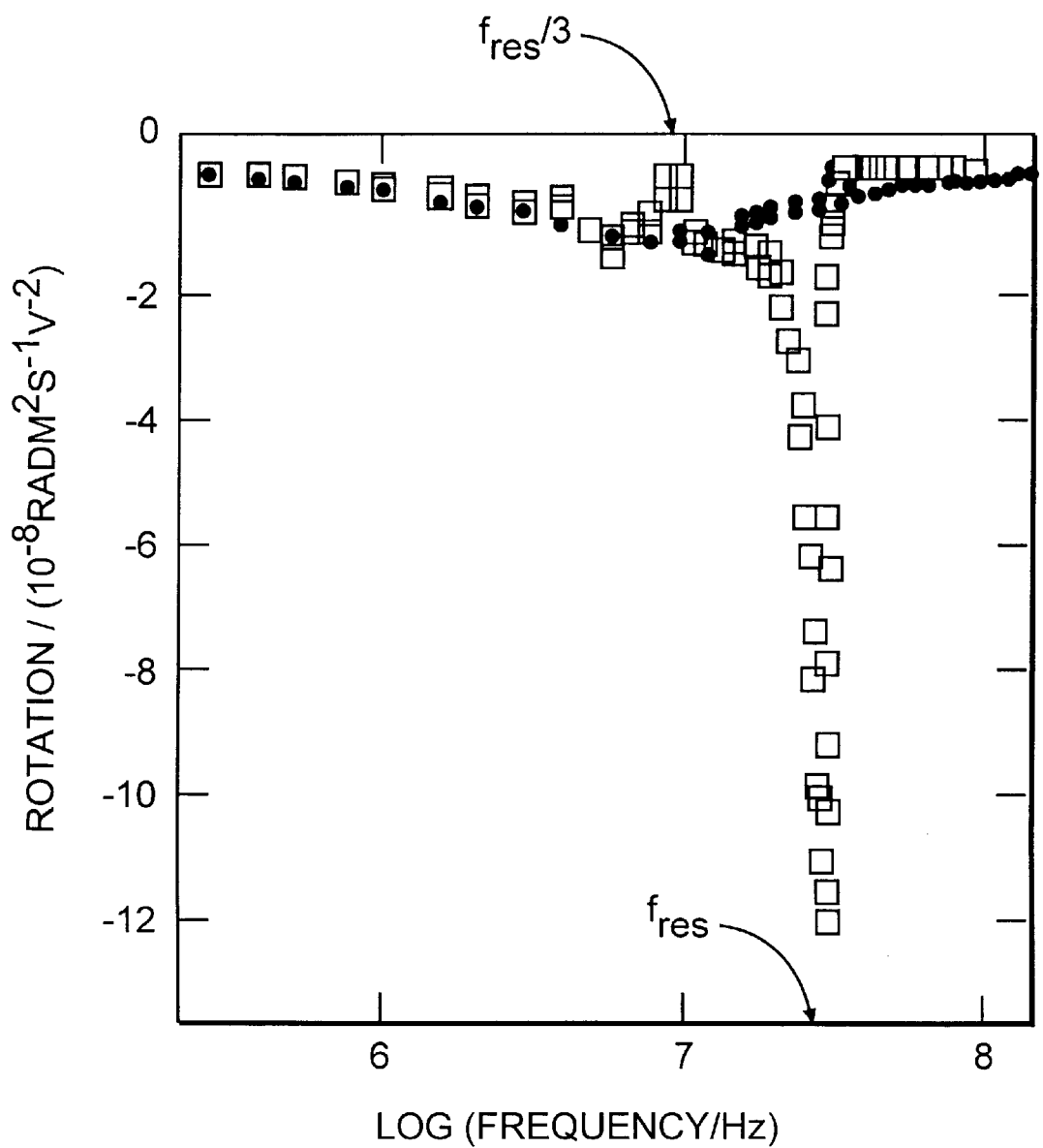
FIG. 3 shows the rotation speed spectrum of sephadex particles of 70 $\mu$m diameter.

FIG. 3 shows the rotation speed spectrum of sephadex particles of 70 $\mu$m diameter. A microchamber according to FIG. 1 was used for measurement, driven by four square-wave signals of 2 $V_{PP}$ offset in phase by 90°. The interval between two opposing electrodes was 100 $\mu$m, and a watery solution was used. When driven by a voltage constant over the entire frequency range, a Lorentz spectrum was obtained (●). After integration of inductive and capacitive elements on the microchamber chip one obtains the spectrum altered by resonance phenomena within the central area of the microchamber (□). What is especially noticeable here is the increase in angular momentum at the resonant frequency $f_{res}$ by a factor of more than 30, and its reduction at a third of $f_{res}$. This reduction is due to the resonance amplification of the third harmonic at the test frequency ⅓ $f_{res}$. The cause of this is the opposing sense of the third harmonic compared to the fundamental.

The quadrupole electrode system illustrated in FIGS. 1, 2 and 3 is suitable for centering or holding a particle or aggregation of particles, especially at the resonant frequency, and also for measuring individual particles (e.g. cells) in the rotating field. The rotational speed of the particle increases very sharply and evidently at resonance as a function of the rotation frequency of the field. If squarewave fields are applied, harmonics of the fundamental appear and thus further resonance in the frequency layers of the forces acting upon the particles.

Figure 4A:
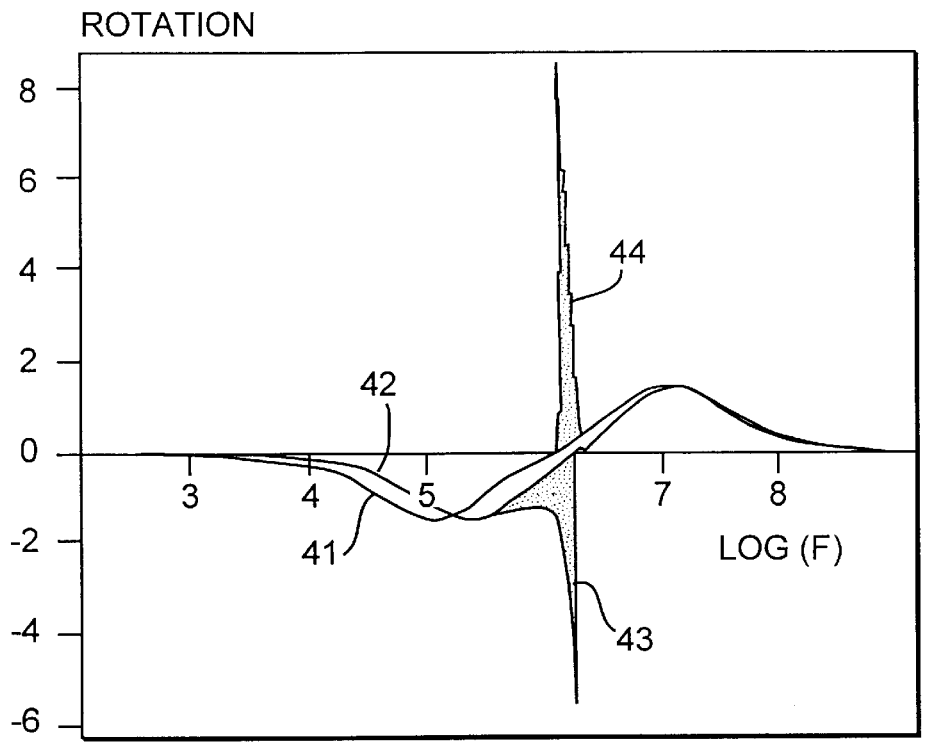
FIGS. 4A and 4B show the influence of a resonance on the rotation of two dielectric particles of slightly different characteristics.
Figure 4B:
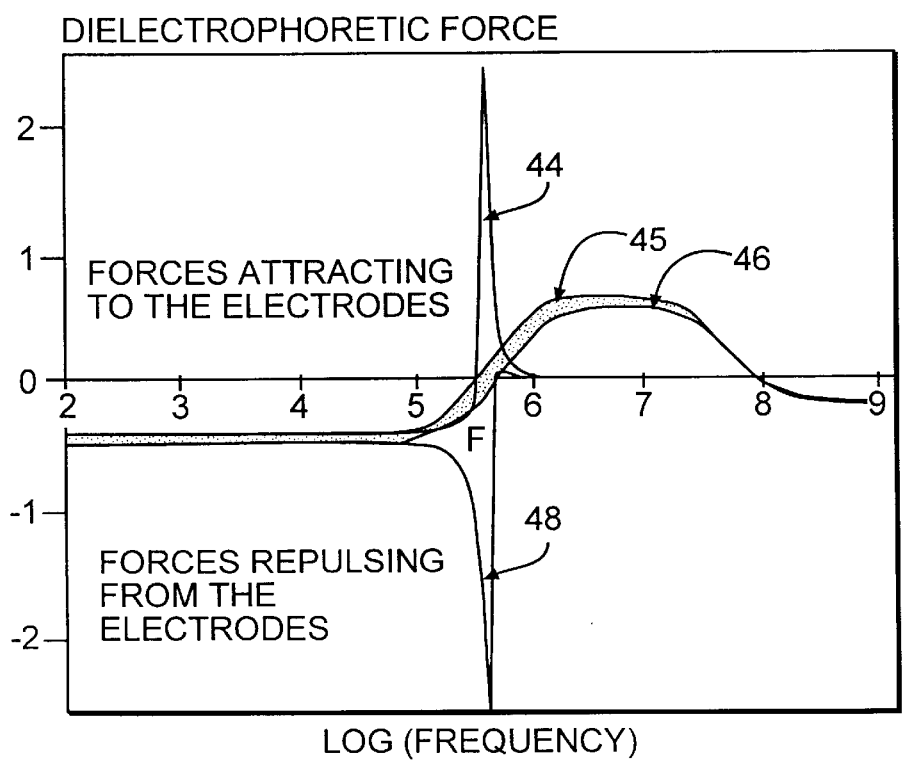

FIGS. 4A and 4B show the influence of a resonance on the rotation of two dielectric particles (here living cells of vegetable or animal origin) of slightly different characteristics (dielectric constant and/or conductivity) and thus the differentiation of microscopic particles in the high-frequency rotating field. Curve 41 is the rotation (rot= rotational speed as a function of the rotational frequency of the field (f)) without resonance for the particle of type 1 (e.g. a cell 1). There is rotation of the cell both opposite to the sense of the field (low frequencies) and in the sense of the rotating field (high frequencies). Curve 42 shows the corresponding effect for a particle of type 2 (e.g. a cell 2). If the resonance is in the vicinity of the zero crossing of the two rotation spectra, the transition in rotation (change of direction) becomes extremely sharp (curve 42→curve 43, curve 41→curve 44). Under these conditions the differences in the dielectric characteristics of the two particles are made use of to move them fast in different senses of rotation. The advantage of this in conjunction with resonance is that particles which only differ slightly in their rotation spectrum in this frequency range nevertheless rotate opposite to one another as in curves 43 and 44. Consequently the particles are very easily identified and separated. Particles in traveling electric fields would exhibit the same response, and here the opposed movement of the particles at resonant frequency can be used directly for separation.

FIG. 4B shows the same resonance effect of the dielectrophoretic forces that drive a particle in the field gradient (45—force spectrum of cells of type 1, 46—force spectrum of cells of type 2, 47—alteration of spectrum upon appearance of resonance of cell of type 1, 48—alteration of spectrum upon appearance of resonance of cell of type 2).

Figure 5:
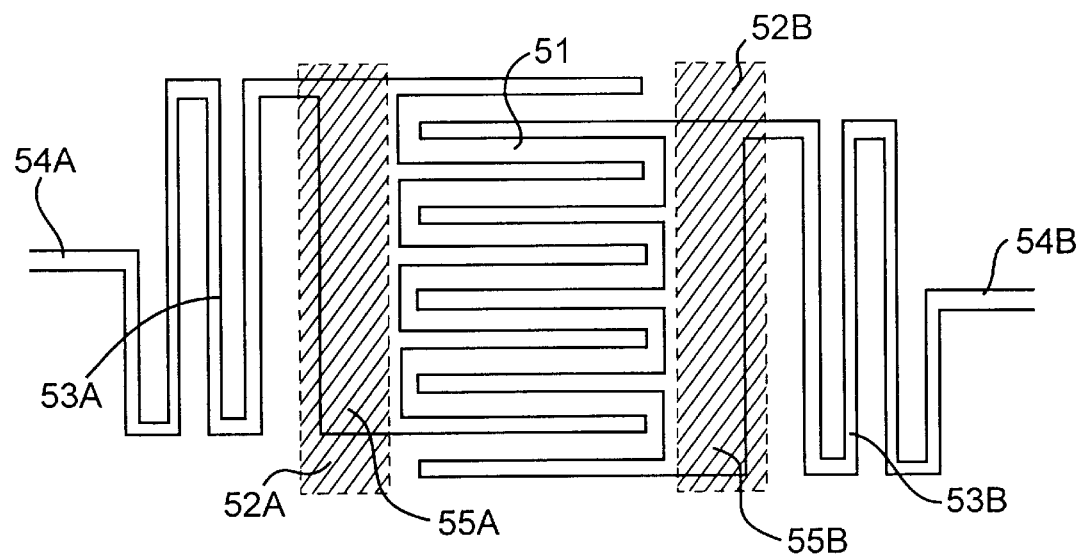
FIG. 5 presents a resonant structure in which the region 51 is kept free of cells and particles by an electric field.

FIG. 5 presents a resonant structure in which the region 51 is kept free of cells and particles by an electric field. The resonant arrangement of inductances 53A and 53B and capacitances 55A and 55B is used to amplify the field in the region 51. The constantly present capacitance of the comb structure 51 is increased by underlaying the electrodes with the dielectric 52A and 52B. The region 51 can be of sieve-like design so that the solution passes through the structure while the particles are held back by the electric field. The element 56 can be used as a tuning element to adjust the resonant frequency. It is processed on the substrate or shifted micromechanically or by other means over the regions 52 causing capacitive changes that tune the oscillating circuits.

Figure 6:
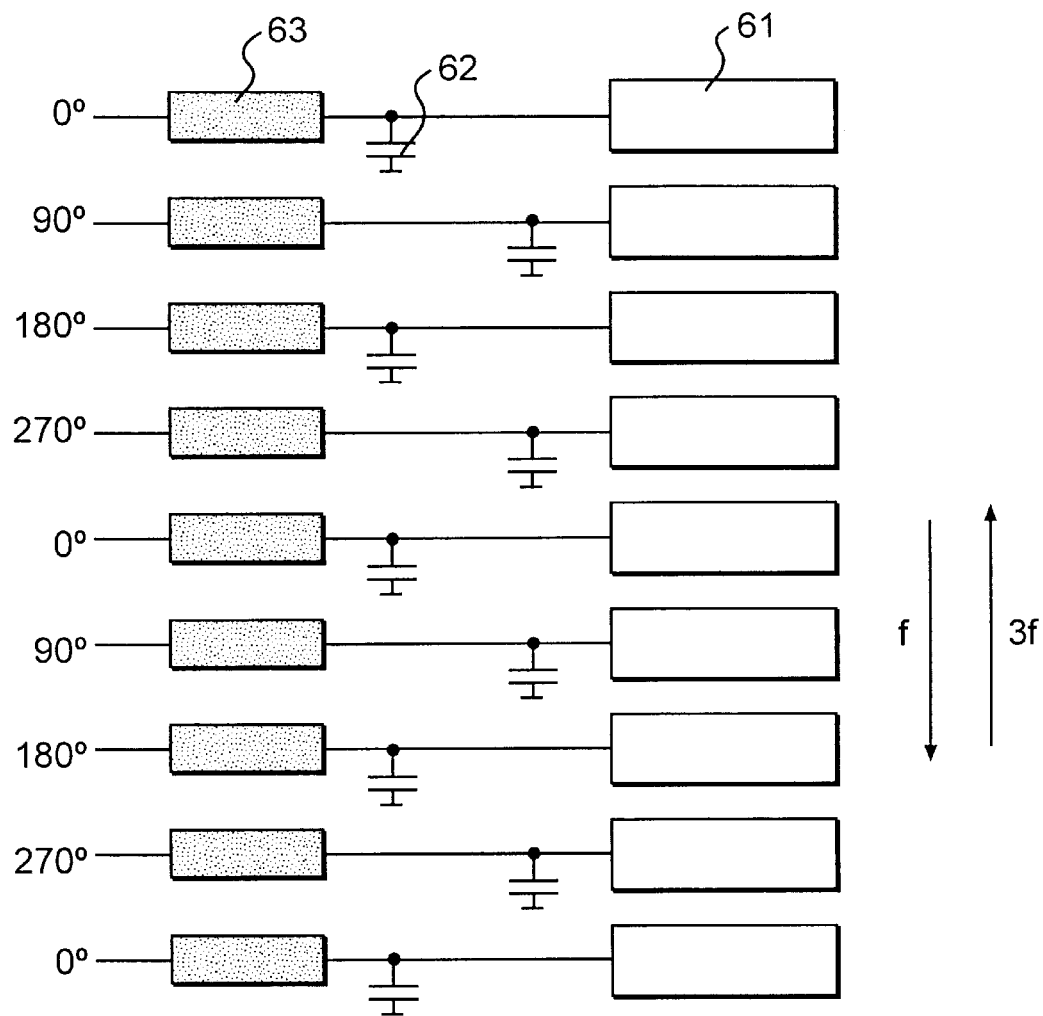
FIG. 6 shows a traveling-wave dielectrophoretic structure.

FIG. 6 shows a traveling-wave dielectrophoretic structure. Particle motion is induced between and/or over the comb-like arrangement of microelectrodes 61. If the structure is driven by mixed sinusoidal signals (e.g. squarewave signals with a duty factor of 1:1) according to the gives phase, the inductances 63 and capacitances 62 can be designed so that the required harmonic of the control signal is amplified by resonance. In this way it is possible, for example, to give this harmonic the same amplitude in the comb structure as the fundamental. Depending on the phase relation of the harmonic frequencies, two opposed traveling fields of a certain frequency relation (e.g. f and 3*f) can he induced for instance.

Figure 7:
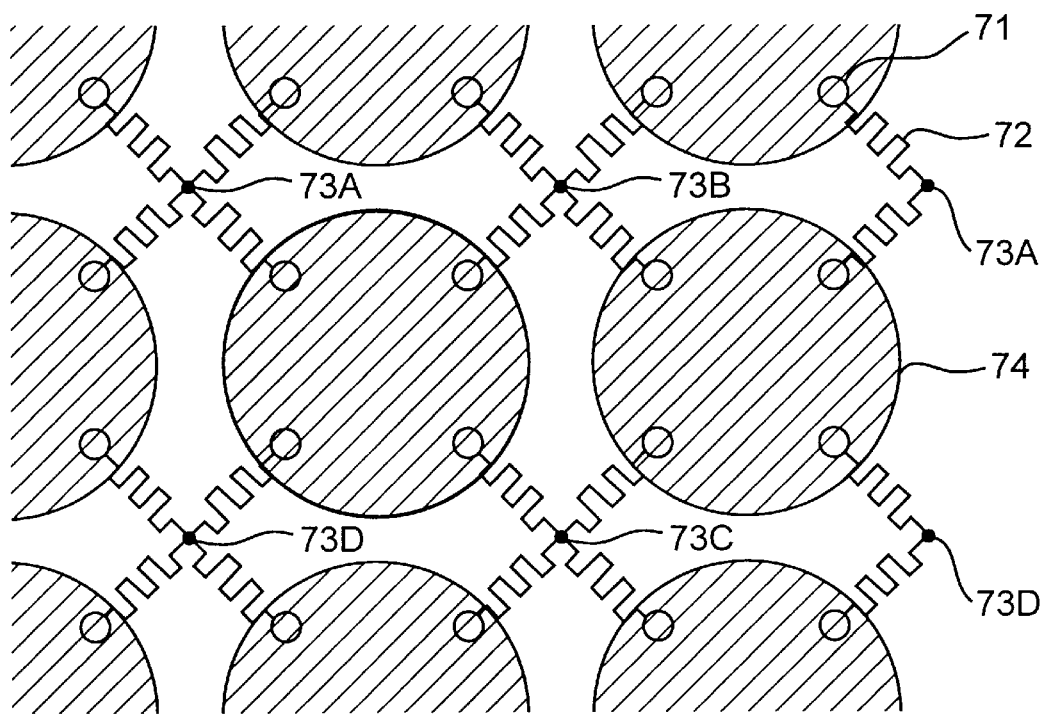
FIG. 7 shows a planar matrix resonant structure for particle and cell handling.

FIG. 7 is a planar matrix resonant structure for particle and cell handling. A large quantity of particles or cells of a suspension can be handled simultaneously in this structure. The suspension in the regions 74 has electrical contact to the electrodes 71, direct or by way of a capacitively acting insulating layer. To drive the structure, four signals offset in phase by 90° are applied to the points 73A, 73B, 73C and 73D. Connection with suitable inductances 72 produces an increase in field strength resonance and corresponding amplification of the field forces on individual particles or cells in the solution regions 74. The number of particles in each solution region 74 influences resonance within this solution region and leads to a decrease in the field forces acting upon further particles for example. This response in the proposed structure makes it possible to fill all solution regions equally.

Figure 8:
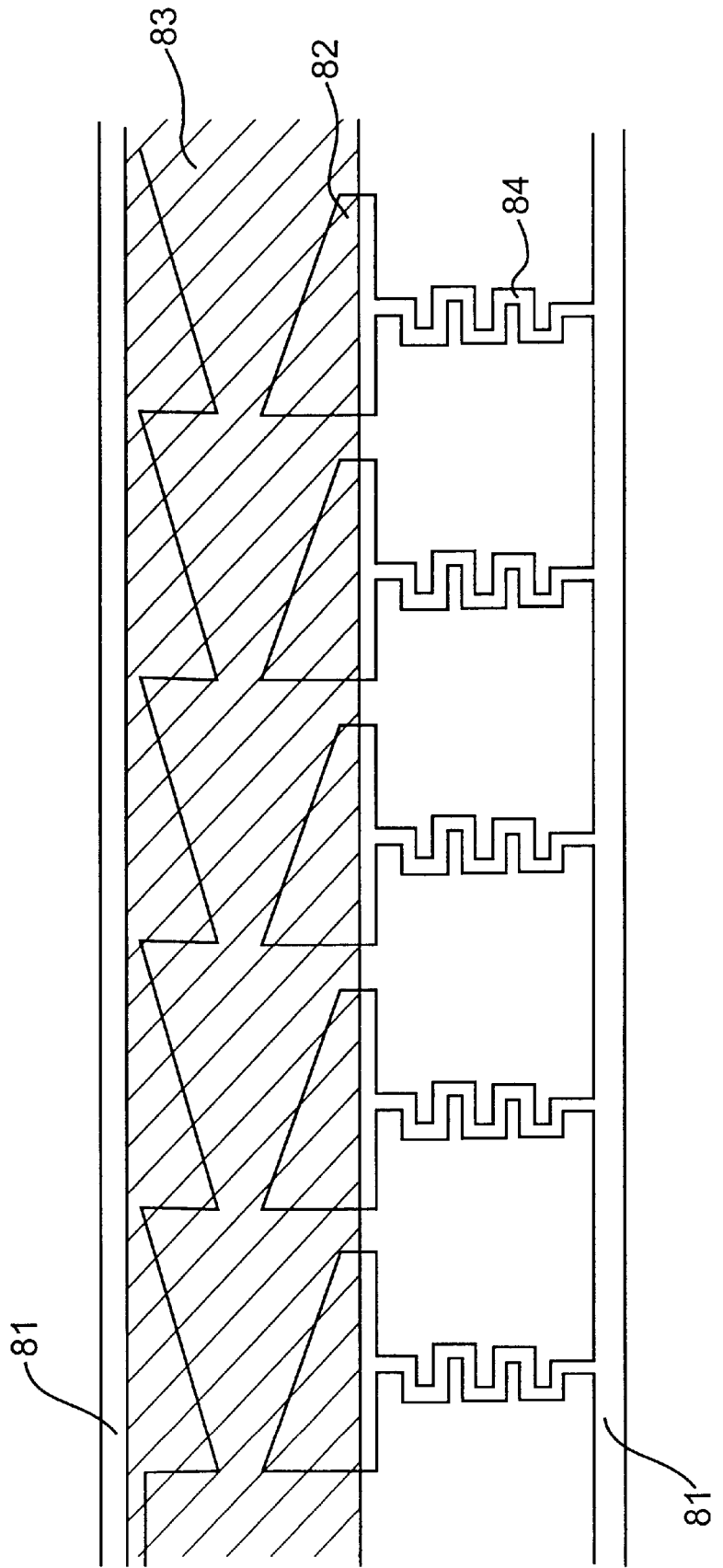
FIG. 8 shows a resonant structure for separating suspended particles or cells in a solution channel 83 by diffusion and field forces.

FIG. 8 shows a resonant structure for separating suspended particles or cells in a solution channel 83 by diffusion and field forces. The structure is driven pulsed or continuously through the leads 81 and 84 so that the particles or cells travel along the channel 83 in motion induced alternately by diffusion and field force. Particles with a high diffusion coefficient and low positive dielectrophoresis will travel especially fast. If the structure is operated so that the suspension means sets the capacitance of the electrodes 82 referred to the common counter-electrode so that there is an increase in the resonance of the field, the presence of particles would alter this capacitance and reduce the field strength here. In this way diffusion predominates over the collecting field forces and undesired accumulations of the particles or cells that are to be separated are thus avoided.

There are uses for the invented device in the sorting and separating of particle mixtures, in medical, biological, biotechnical, physical and chemical applications, especially in conjunction with the verification, characterization and identification of cells, organelles, viruses and macromolecules, in the powering of dielectric micromotors or microactuators of a rotation or linear type, in the directing, sorting, measuring, positioning, destruction and modification of suspended particles, in microhandling devices, in the assembly and encapsulation of pharmaceutical products, in the shaping of microparticles, in microchemistry (especially for synthesizing fluid or solid phases, which can be held, combined, made to react, divided and/or separated by the resonance principle of the invention), or in combination with spectroscopic methods of measurement (especially with the fluorescence correlation spectroscopy described in publication WO 96/16313 or other, in particular confocal fluorescence measurement methods as described in publication WO 96/13744 for example and European patent application no. 96 116 373.0.

We claim:

1. Method for position and/or type-selective control of the position and/or change of position of suspended particles in a multielectrode system by the effect of polarization forces that are induced in the particles by alternating electric fields in the multielectrode system, which particles comprise biological or synthetic objects with dimensions essentially corresponding to those of biological cells or cell organelles, viruses or macromolecules, characterized in that the polarization forces are amplified or reduced by increased resonance or damping of the field strength of the alternating electric fields at certain frequencies in at least one locally demarcated region of the multielectrode system, the alternating electric fields including alternating, rotating or traveling electric fields so that, in circular and/or linear multielectrode configurations, there is rotation, translation or positioning of particles induced by the principle of electrorotation, dielectrophoresis, levitation or traveling-wave technology, whereby certain frequency ranges of the particular motion are amplified or damped by the resonance phenomena.

2. Method according to claim 1 in which the resonant change of field strength is achieved by the external adjustment of controllable components provided in the multielectrode system.

3. Method according to claim 1 in which the resonant increase of field strength is influenced selectively by the passive electrical characteristics of the particle suspension, whereby, especially through the presence or passage of one or more particles in a region in the multielectrode system, the electrical characteristics of the suspension at this point are altered so that the resonant response of the microstructure is altered, defined or electronically tuned so that the resonance conditions, possibly selective in time through alteration of the passive electrical characteristics of the suspension, are only achieved or terminated until the presence or passage of a certain particle type by this particle itself.

4. Method according to claim 1 in which the resonant increase of field strength is achieved at a certain fundamental of the alternating electric fields and/or multiples of the fundamental with amplification by a factor of approx. two to 1000, whereby in particular the alternating electric fields are generated by periodic control voltages of a frequency $\geq 100$ Hz with amplitudes between 0.1 and 200 V and the periodic signals applied for field generation can be sinusoidal, triangular, squarewave, tristate or combinations of these signals, of which certain Fourier components are possibly amplified by the resonance, which Fourier components of the periodic control signal can simultaneously generate field components of different rotation or translation sense, whereby the amplitudes of the Fourier components of the field can be attuned to one another by the resonance.

5. Method according to claim 1 in which holding of the particles is amplified or damped by the resonance phenomena.

6. Method according to claim 1 in which the particles comprise a mixture of different types of particles and the resonances alter the motion of part or all of these particle types, whereby one or more particle types alter from negative to positive dielectrophoresis at the resonant frequency or the sense of particle rotation or motion in the traveling-wave field.

7. Method according to claim 1 in which two or more field frequencies are modulated or used simultaneously by different electrode subsystems or used alternating with the same or opposite sense of rotation or translation and adjustable amplitude in that the resonant frequency is applied to ranges of the dielectric particle spectrum (force as function of frequency) where the particle types differ.

8. Device for position and/or type-selective control of the position and/or change of position of suspended particles in a multielectrode system by the effect of polarization forces that are induced in the particles by alternating electric fields in the multielectrode system, which particles comprise biological or synthetic objects with dimensions essentially corresponding to those of biological cells or cell organelles, viruses or macromolecules, characterized in that the multielectrode system forms with the particle suspension an electrical network, in which resonance means are provided for creating a resonant increase or damping of the field strength of the alternating electric fields at certain frequencies in at least one locally demarcated region of the multielectrode system, resonance means being formed by the capacitive and/or inductive design of the electrodes of the microelectrode system.

9. Control device according to claim 8 in which means the resonance are formed by controllable components integrated into or added to the multielectrode system.

10. Control device according to claim 8 in which the resonance means are formed by the particle suspension, especially the particles themselves as components of the electrical network.

11. Control device according to claim 8 in which the microelectrode configurations exhibit typical gap dimensions from 10 nm to several hundred μm and in which rotating or alternating electric fields are generated.

12. Control device according to claim 8 in which the microelectrode configurations have three-dimensional structures or multilayer structures on a substrate consisting of glass, semiconductor material, plastic or ceramic.

13. Control device according to claim 8 in which the substrate has structures, passive components, areas with channels, walls, trenches, cutouts or barriers, and/or micromechanical elements like valves, membranes, shiftable elements or moving arms for tuning the oscillating circuits, or in which the output stages or the entire high-frequency generator for producing the electrode signals and/or driving the components to control the resonant frequencies are integrated on the substrate.

14. Control device according to claim 8 in which several microelectrode systems are configured next to one another, back to back, offset, facing one another, as a cascade, in a ring or stacked.

15. Control device according to claim 8 in which components are provided with which the resonant frequencies are controlled and which can be operated by a control program, which components are formed of active components like variable-capacitance diodes, field-effect transistors and adjustable inductors, whereby the alterations in the resonance phenomena can also be generated by connecting, disconnecting or bypassing components of the oscillating circuits.

16. Control device according to claim 8, in which the electrodes on essentially planar, insulating mounts form at least an open electrode system that has capacitive, inductive and resistive components and is connected through the particle suspension solution to at least one network-type oscillating circuit system.

17. Control device according to claim 16, in which the electrode system takes the form of meanders and/or loops covered by the insulating layers, which form networks with altered influence of capacitive and/or inductive elements, whereby separate resonance regions influence one another.

18. Method for position and/or type-selective control of the position and/or change of position of suspended particles in a multielectrode system by the effect of polarization forces that are induced in the particles by alternating electric fields in the multielectrode system, which particles comprise biological or synthetic objects with dimensions essentially corresponding to those of biological cells or cell organelles, viruses or macromolecules, characterized in that the polarization forces are amplified or reduced by increased resonance or damping of the field strength of the alternating electric fields at certain frequencies in at least one locally demarcated region of the multielectrode system, two or more field frequencies being modulated or used alternating with the same or opposite sense of rotation or translation and adjustable amplitude in that a resonant frequency is applied to ranges of the dielectric particle spectrum of said particles where the particle types differ.

19. Device for position and/or type-selective control of the position and/or change of position of suspended particles in a multielectrode system by the effect of polarization forces that are induced in the particles by alternating electric fields in the multielectrode system, which particles comprise biological or synthetic objects with dimensions essentially corresponding to those of biological cells or cell organelles, viruses or macromolecules, characterized in that the multielectrode system forms with the particle suspension an electrical network, in which resonance means are provided for creating a resonant increase or damping of the field strength of the alternating electric fields at certain frequencies in at least one locally demarcated region of the multielectrode system, the electrodes on essentially planar, insulating mounts forming at least an open electrode system that has capacitive, inductive and resistive components connected through the particle suspension solution to at least one network-type oscillating circuit system, the electrode system being in the form of meanders and/or loops covered by the insulating layers, which form a network with altered influence of capacitive and/or inductive elements, whereby separate resonance regions influence one another.

* * * * *